(12) United States Patent
Van Baarle (10) Patent No.: US 10,536,649 B2
(45) Date of Patent: Jan. 14, 2020

(54) IMAGE SENSOR TILE AND IMAGE SENSOR

(71) Applicant: Teledyne Dalsa B.V., Eindhoven (NL)

(72) Inventor: Bart Van Baarle, Breda (NL)

(73) Assignee: TELEDYNE DALSA B.V., Eindhoven (NL)

( * ) Notice: Subject to any disclaimer, the term of this patent is extended or adjusted under 35 U.S.C. 154(b) by 152 days.

(21) Appl. No.: 15/744,576

(22) PCT Filed: Apr. 22, 2016

(86) PCT No.: PCT/NL2016/050287
§ 371 (c)(1),
(2) Date: Jan. 12, 2018

(87) PCT Pub. No.: WO2017/183959
PCT Pub. Date: Oct. 26, 2017

(65) Prior Publication Data
US 2018/0213163 A1    Jul. 26, 2018

(51) Int. Cl.
*H04N 5/32* (2006.01)
*H01L 27/146* (2006.01)
(Continued)

(52) U.S. Cl.
CPC ............ *H04N 5/32* (2013.01); *A61B 6/4233* (2013.01); *H01L 27/14607* (2013.01);
(Continued)

(58) Field of Classification Search
CPC ...... H04N 5/32; H04N 5/3559; H04N 5/3658; H04N 5/376; H01L 27/14607; H01L 27/14658; A61B 6/4233
(Continued)

(56) References Cited

U.S. PATENT DOCUMENTS 7,952,077 B2 *   5/2011   Tashiro .................. G01T 1/2928
                                                    250/370.09
8,417,863 B2 *   4/2013   Lee .......................... G06F 1/10
                                                    710/300
(Continued)

FOREIGN PATENT DOCUMENTS

EP            2879376 A1   6/2015
EP            3007435 A1   4/2016
WO   WO 2015/049994 A1   4/2015

OTHER PUBLICATIONS

International Search Report and Written Opinion of the International Searching Authority for International Application No. PCT/NL2016/050287 dated Sep. 8, 2016.
(Continued)

*Primary Examiner* — Seung C Sohn
(74) *Attorney, Agent, or Firm* — K&L Gates LLP (57) ABSTRACT

The present invention is related to an image sensor tile and to an image sensor comprising such a tile.
An image sensor tile comprises a plurality of pixels that are arranged in a pattern of rows and columns.
According to the present invention, each pixel block comprises, for each pixel row, at least one restoring unit that is arranged in a single pixel in that row or at least one restoring unit that is distributed over pixels in that row, said at least one restoring unit being configured to restore a shape of the at least one control signal.

22 Claims, 10 Drawing Sheets

(51) Int. Cl.
  *A61B 6/00* (2006.01)
  *H04N 5/355* (2011.01)
  *H04N 5/365* (2011.01)
  *H04N 5/376* (2011.01)
(52) U.S. Cl.
  CPC ..... *H01L 27/14658* (2013.01); *H04N 5/3559* (2013.01); *H04N 5/3658* (2013.01); *H04N 5/376* (2013.01)
(58) Field of Classification Search
  USPC .................................................. 250/208.1
  See application file for complete search history.

(56) References Cited

U.S. PATENT DOCUMENTS

2014/0168491 A1   6/2014   Totsuka
2015/0103973 A1   4/2015   Liu et al.

OTHER PUBLICATIONS

European Patent Office Examination Report for European Application No. 16732001.9 dated Aug. 14, 2019.

\* cited by examiner

IMAGE SENSOR TILE AND IMAGE SENSOR

This application is a national stage application claiming priority to and the benefit of International Application No. PCT/NL2016/050278, filed Apr. 22, 2016.

The present invention is related to an image sensor tile and image sensor comprising such a tile.

Image sensors are known in the art. A particular example is an X-ray sensor. This type of sensor can for instance be used in medical imaging, wherein the patient is arranged in between an X-ray sensor and an X-ray source.

Within the concept of the present invention, an image sensor tile comprises a substantially planar device, preferably having a rectangular or square shape although the image sensor tile may have a curved shape. For example, for mammography a rounded or curved detector is preferred as this would better match the chest wall.

An image sensor tile comprises photosensitive components, as well as at least a part of the electronic circuitry required for control and read-out. Within the context of the present invention, photosensitive components relate to components that are sensitive to electromagnetic radiation including infrared light, visible light, ultraviolet light, and X-rays. The image sensor tiles can for instance be manufactured using known semiconductor processes. As an example, an image sensor, such as an X-ray sensor, can be manufactured using a CMOS process, wherein the corresponding image sensor tile comprises a plurality of photosensitive pixels that are arranged in rows and columns. For X-ray sensors, a scintillator layer may be used that converts incoming X-rays into visible light. This light can be sensed by each photosensitive pixel although the pixel may itself be configured to detect the X-rays, e.g. without using a scintillator layer.

The photosensitive pixel may comprise a photosensitive diode, such as a (pinned) photodiode, and a storage capacitor. The charges that are generated as light falls onto the photodiode are accumulated on the storage capacitor. By sensing the voltage at the storage capacitor, the amount of light, such as visible light or X-rays, corresponding to the pixel can be determined.

A semiconductor-based sensor, such as a CMOS sensor, can have a photoactive surface that exceeds the size of the available semiconductor wafers. These sensors then comprise a plurality of butted image sensor tiles, wherein each image sensor tile is manufactured using a respective semiconductor wafer or part thereof.

Figure 1A:
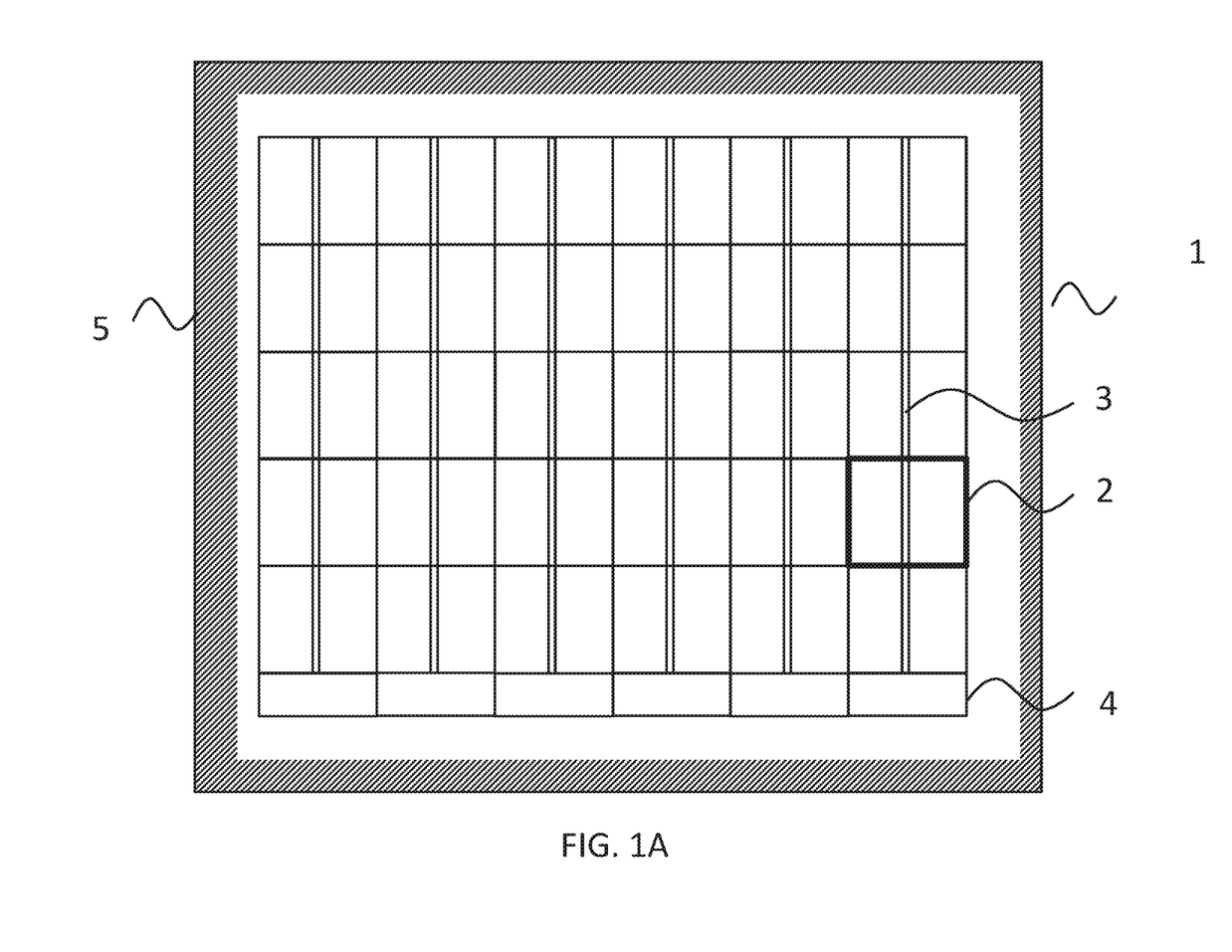
FIGS. 1A and 1B illustrate various aspects of a known X-ray sensor tile.

FIG. 1A illustrates an example of a known X-ray sensor tile 1. It comprises a plurality of identical pixel blocks 2, each pixel block comprising a plurality of photosensitive pixels that are arranged in a pattern of rows and columns. Each pixel block 2 comprises a row driver block 3 that comprises a plurality of row drivers, each row driver in said row driver block being configured for providing at least one logic control signal to pixels that are arranged in a row that is associated with that row driver. For instance, each row driver is configured to select the pixels in its associated row for subsequent read-out.

X-ray sensor tile 1 further comprises read-out circuitry 4 that is configured to read-out a selected row of pixels. Here, it is noted that read-out circuitry 4 is not part of the repetitive arrangement of pixels blocks 2. Finally, a sealing ring 5 is normally arranged around the structures on X-ray sensor tile 1. In case a multi-tile X-ray sensor is manufactured, it may be possible to implement the read-out circuitry only on some of the tiles, for instance the bottom tiles. In this case, there should be an electrical connection between the different tiles in the vertical direction to for instance allow the read-out circuitry to read out the pixels that are part of a selected row in the upper tile. For instance, bond wires could be used to realize the electrical interconnection between the different tiles.

Figure 1B:
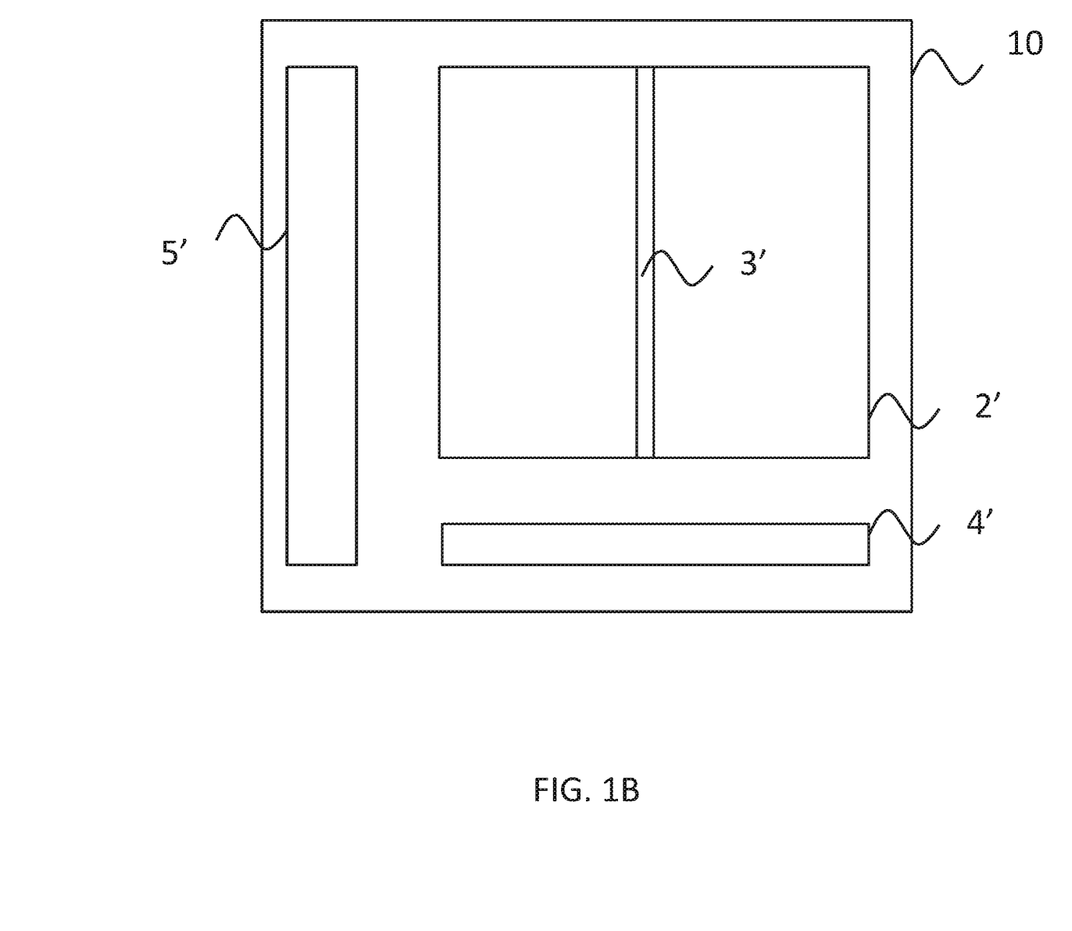

The pixels blocks can be realized using a wafer stepping technique, wherein a plurality of reticles, or parts thereof, are projected onto the wafer. An example of a reticle is illustrated in FIG. 1B. Although the skilled person understands that a single reticle is generally used to define a single layer or processing step, FIG. 1B illustrates that several different regions can be identified within a reticle. For instance, reticle 10 comprises a region 2' for defining pixel blocks 2, wherein region 2' comprises structures 3' for defining row driver blocks 3. Similarly, reticle 10 comprises structures 5' for defining sealing ring 5 and structures 4' for defining read-out circuitry 4.

When using reticle 10 to realize pixel blocks 2, a blading technique is used, wherein structures 5' and 4' are blocked as a result of which only region 2' is projected. In this manner, the aforementioned repetitive arrangement can be achieved.

As can be seen in FIG. 1B, structures 3' for realizing row driver blocks 3 are incorporated inside region 2', which region also comprises structures for realizing the pixels in each pixel block. Consequently, row drivers are present in each pixel block 2.

Figure 2A:
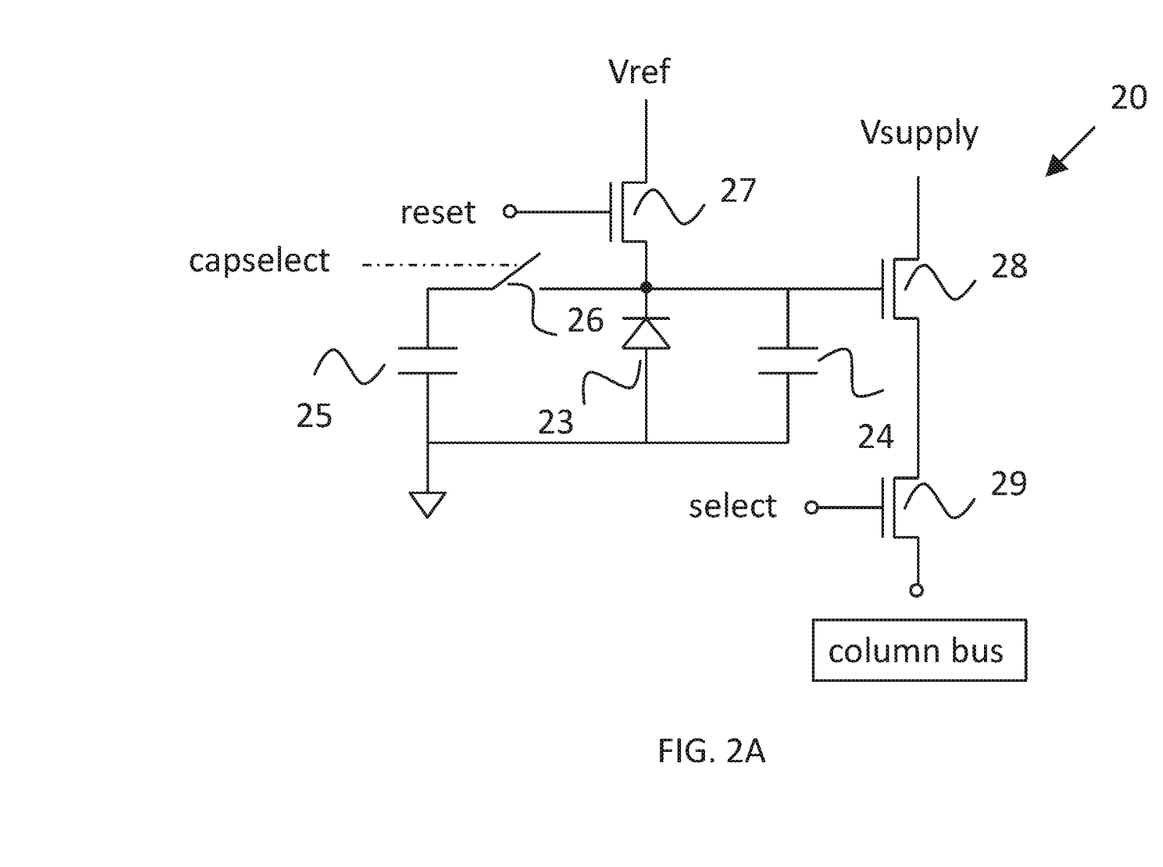
FIGS. 2A-2D illustrate a known 3T pixel schematic, an exemplary signal line configuration, and an exemplary image output.

FIG. 2A illustrates a known schematic for a pixel 20, referred to as a 3T schematic. The pixel comprises a (pinned) photodiode 23, a primary storage capacitor 24, and a secondary storage capacitor 25 which can be switched using a switch 26. Typically, a scintillator layer (not illustrated) is applied over the pixel or is integrated therewith. This layer converts incoming X-rays into visible light which can be detected by photodiode 23.

The operation of the pixel can be explained as follows. As a first step, the voltage at the terminal between capacitor 24 and photodiode 23 is charged/reset to a predefined reference voltage Vref using a NMOST 27 in response to a reset signal received from the row driver. Next, NMOST 27 is brought into in a non-conducting state. When light falls onto photodiode 23, it generates charges which are transferred to capacitor 24. Consequently, the voltage at the terminal of capacitor 24 will decrease depending on the incident light. After a predetermined time, e.g. the integration time, the voltage at this terminal is sensed using a source follower NMOST 28 that is connected to an NMOST 29 that acts as a selection FET. More in particular, in response to a select signal from the row driver, the voltage at the terminal of capacitor 24 is fed through source follower 28 and selection FET 29 to the read-out circuitry. There, the analog signal is converted into a digital value using an analog-to-digital converter. As a final step, selection FET 29 is brought into a non-conductive state and the process is repeated.

By closing switch 26, in response to receiving a capacitance select signal from the row driver, secondary storage capacitor 25 can be put parallel to primary storage capacitor 24. This allows the pixel to process a higher dose of X-rays as the effective storage capacitance has increased, and to thereby offer a different sensitivity.

It is noted that various sensing schemes are known to the skilled person, for instance to correct for a process-related spread in the threshold voltages of the various MOSTs. The present invention is not limited to the particular pixel schematic shown in FIG. 2A, nor to the particular manner of operation described above.

Figure 2B:
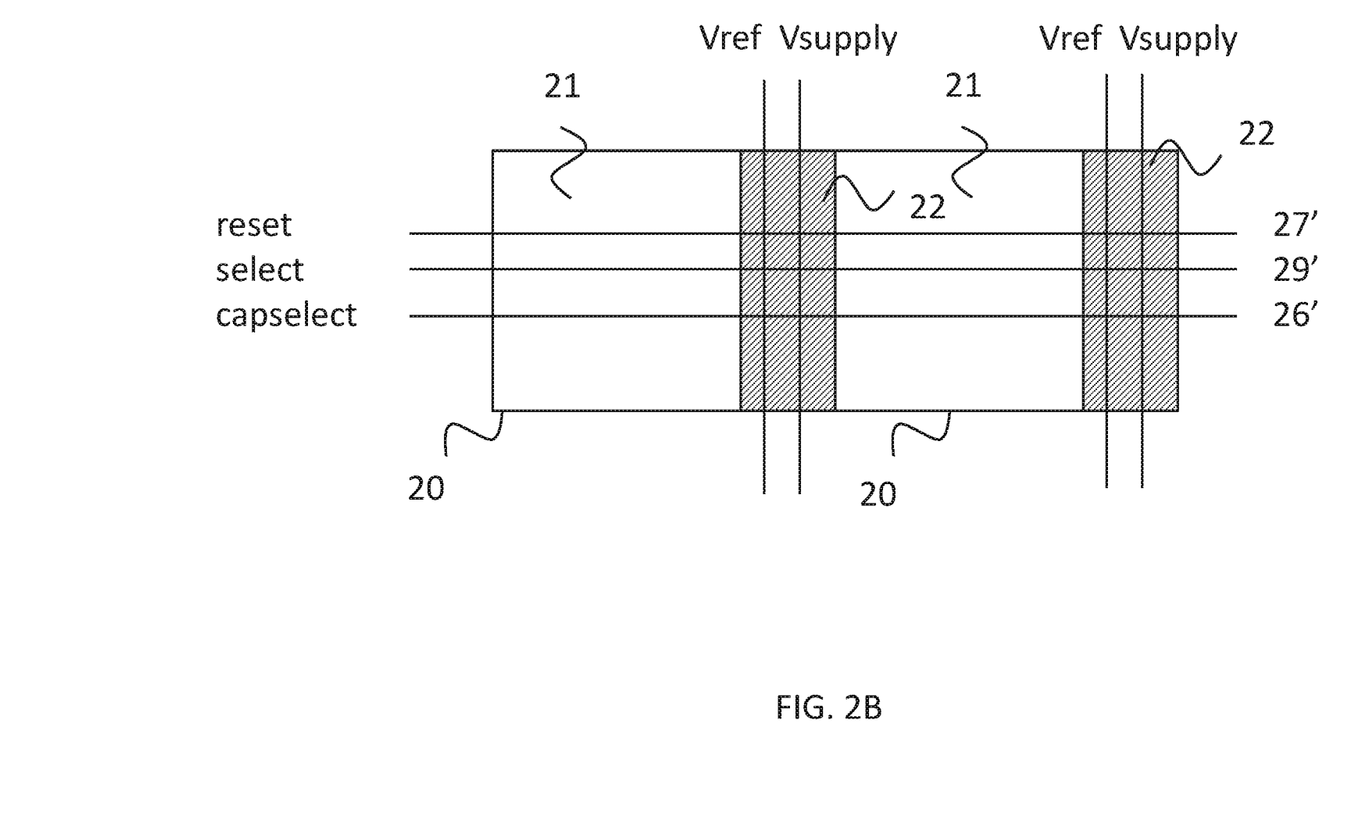

FIG. 2B illustrates two adjacent pixels 20 in a pixel block 2 of X-ray sensor tile 1. Each pixel 20 comprises a photosensitive part 21, determined by photodiode 23, and a photo-insensitive part 22, in which the other components of FIG. 2A are realized. As can be seen, X-ray sensor tile 1 comprises a plurality of control signal lines 26', 27', 29' that are arranged along the row of pixels 20 and which connect to the various switches or FETs inside each pixel as illustrated in FIG. 2A. Also visible in FIG. 2B are the voltage lines for suppling the reference voltage Vref and a supply voltage Vsupply.

Figure 2C:
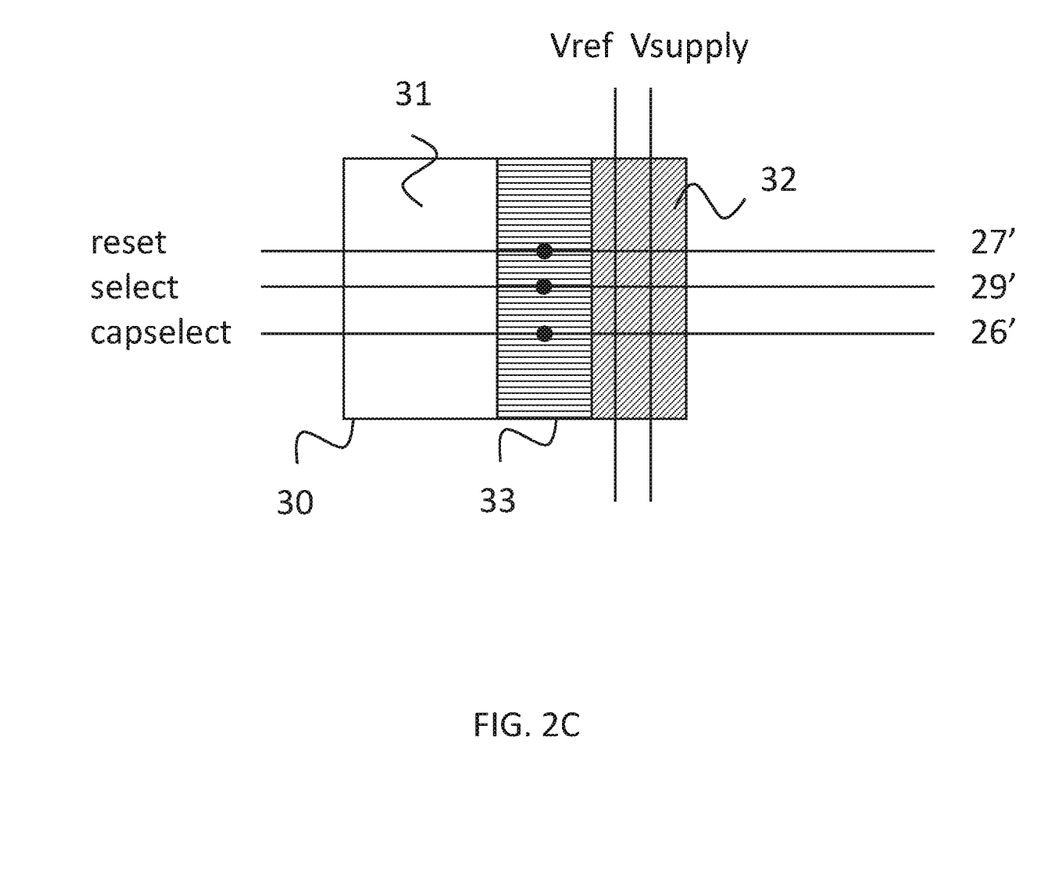

Typically, row drivers are realized within the pixel blocks and within the area of a single pixel, at the expense of the photosensitive area. This is illustrated in FIG. 2C. Here, a pixel 30 is shown that comprises a photosensitive part 31, and two photo-insensitive parts 32, 33. In this case, the photosensitive diode is realized in part 31, whereas the other components of the schematic in FIG. 2A are realized in part 32 in a manner similar to FIG. 2B. However, pixel 30 additionally comprises a part 33 in which a row driver 3 is implemented. As can be seen by comparing FIGS. 2B and 2C, the size of the photodiode in pixel 30 is smaller than the photodiode in pixel 20. For relatively small pixels, a situation may therefore occur wherein the row driver occupies most of the space in the pixel, or occupies the pixel in its entirety, such that there is limited to no area available for the photodiode. Such pixel can therefore only partially contribute information for generating the final X-ray image or not contribute any information at all.

Figure 2D:
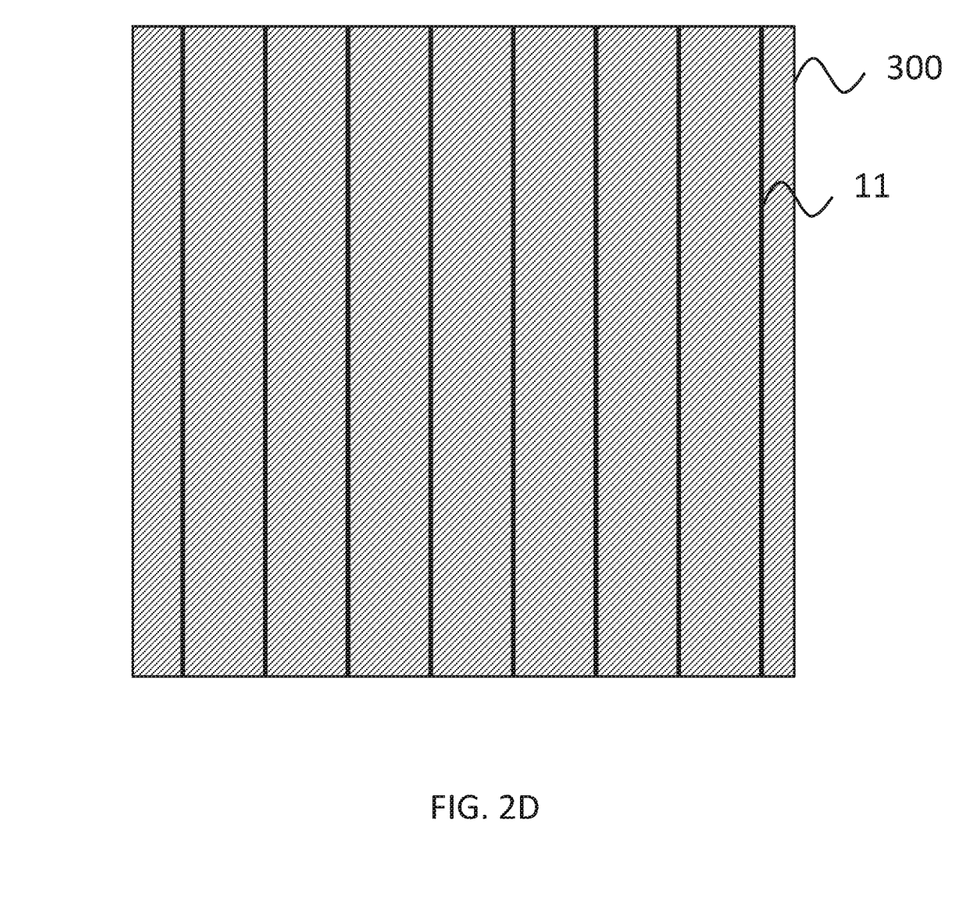

A typical raw or uncorrected output 300 of X-ray sensor tile 1 is illustrated in FIG. 2D. Here, darker lines 11 indicate the presence of row drivers 3. In these lines, less X-rays are detected due to the smaller photodiodes. These artefacts need to be corrected during image post-processing, which is not always possible, particularly when the row drivers leave no room for a photodiode to be arranged in a pixel.

Another drawback of the X-ray sensor tile in FIG. 1A is that this tile is susceptible to column defects. The source contacts of select FETs 29 of all pixels in a given column are connected to each other. Hence, if for instance a short or defect occurs near select FET 29, the entire column may become unusable, resulting in a column defect. Depending on the maximum number of allowable column defects, a tile might be considered as a fail, lowering yield figures. In general, a row driver column can be accounted for as a non-functional column or partially functional column. It is therefore desired to reduce the number of row driver columns as much as possible.

It is an object of the present invention to provide a solution to these problems. This object has been achieved with the image sensor tile as defined in claim 1 which is characterized in that each pixel block comprises, for each pixel row, at least one restoring unit that is arranged in a single pixel in that row or at least one restoring unit that is distributed over pixels in that row, said at least one restoring unit being configured to restore a shape of the at least one control signal.

An advantage of using a restoring unit is that it allows a reduction in the number of row drivers without degrading signal integrity of the various control signals. Furthermore, the restoring unit can be realized in a relatively small area. Depending on pixel size and/or pitch, such area is normally available in each pixel without sacrificing photosensitive area.

The present invention therefore proposes a solution in which the number of row drivers can be reduced, thereby gaining photosensitive area. Moreover, because the total number of row drivers can be reduced, the problem of column defects is alleviated.

At least one pixel in each pixel block may be photosensitive. Additionally or alternatively, each row driver block may comprise, per row, a plurality of further pixels that are substantially identical to the pixels in the pixel blocks, wherein the row driver for that row is further configured for providing at least one logic control signal to said further pixels. By incorporating pixels in the row driver blocks, a situation can be avoided wherein two row driver blocks are adjacently arranged on the X-ray sensor. This situation may for instance occur when two tiles having row driver blocks at the edges are arranged next to each other. Such configuration may otherwise result in a relatively large region on the X-ray sensor having no or a very limited amount of photosensitive pixels.

The row driver block may correspond to a first sub-field of a reticle set and the pixel blocks may correspond to a second sub-field of that same reticle set, different from the first sub-field. Consequently, several pixel blocks may be arranged next to each other without an interposed row driver block. Such row driver block may for instance be arranged next to a plurality of pixel blocks. In this case, compared to the tile depicted in FIG. 1A, the row driver is no longer part of the pixel block. Consequently, a relatively large number of pixels distributed over a plurality of pixel blocks need to be driven by a limited number of row drivers. For example, a single row driver is arranged left to the row of pixels that need to be driven by that row driver. When a square arrangement of for example 6×6=36 reticle pixel blocks is used, each having a width and height of for example 20 mm and comprising for example 100 pixels having a width of 200 micrometer, then each row driver must drive 600 pixels instead of the 100 pixels that would need to be driven in prior art approaches. The control signals are supplied via signal lines, which are mostly embodied as relatively thin metal tracks. These tracks are connected to the transistors, e.g. MOST, which are used inside the pixel for instance to reset or select a pixel. More in particular, the thin metal tracks are connected to the voltage-dependent capacitances of the FETs, such as for instance the gate-source capacitance. As a result, the thin metal tracks constitute voltage-dependent ladder-type RC networks. When a control signal is provided to the thin metal track by the row driver it propagates through the RC network. During this propagation the shape of the control signal will change, affecting rise and/or fall times. This shape distortion causes inconsistences in the timing of the various pixels. For instance, the pixel closest to the row driver may be selected or reset much quicker than the pixel that is farthest from the row driver. Furthermore, the timing is affected by the voltage-dependency of the capacitances in the RC network. Moreover, the integration times, i.e. the time during which the pixel accumulates charges in the storage capacitor, may differ between these pixels. However, this problem may be solved because each pixel block may comprise, for each row, a restoring unit distributed over one or more pixels in that row and being configured to restore a shape of the control signal. In this case, the shape of the control signal is restored as it propagates through the row of pixels. This shape restoration prevents, or at least considerably reduces, the occurrence of image artefacts due to the deterioration of the control signal. Also, compared to known image sensor tiles, it is possible to reduce the delay and/or settling times that have to be used after applying the control signals. Delay and/or settling times are for instance used to ensure that all pixels in a given row are read-out or reset before applying a next control signal. According to the invention, these times can be reduced thereby speeding up readout times and framerates.

The image sensor tile may comprise an arrangement of adjacently arranged pixel blocks, wherein a row driver block is arranged on at least one side of said arrangement. For example, denoting a pixel block by P and a row driver block by D, the following arrangements may be obtained: D-P-P or D-P-P-D.

Alternatively, the image sensor tile may comprise an arrangement of a row driver block that is adjacently arranged to a pixel block on either side of the row driver block. For example, the following arrangement may be obtained: P-D-P or P-D-P-P-D-P.

Alternatively, the image sensor tile may comprise an alternating arrangement of a pixel block and a row driver block. For example, the following arrangement may be obtained: P-D-P-D.

The arrangements mentioned above are preferably repetitive arrangements. Moreover, these arrangements can be mixed to provide new arrangements.

Each row driver may be configured to provide a plurality of logic control signals, wherein a restoring unit is arranged for each logic control signal or wherein the restoring unit is configured to restore the shape of each control signal. For instance, if the three control signals are used for each row as depicted in 2B, three separate restoring units can be used. Alternatively, a single restoring unit can be used that restores the shape for each control signal separately. However, it is noted that not every control signal may be critical, so application of the restoring unit may be limited to only those control signals that are critical.

Each pixel may comprise a light-sensitive part and a part that is substantially insensitive to light. The restoring unit may then be arranged in the light insensitive part of the one or more pixels. Consequently, little or no adverse effects with respect to light output are related to the implementation of the restoring unit.

Further to the above, each pixel may comprises a photosensitive diode, a first storage capacitor for receiving electric charges from the photosensitive diode, and a reset transistor for resetting, in response to a reset signal, a voltage at one of the terminals of the storage capacitor to a predefined voltage. The at least one control signal, of which the shape is restored by the restoring unit, may comprise the reset signal. Furthermore, each pixel may further comprise a second storage capacitor that can be switched, in response to a capacitance select signal, in parallel to the first storage capacitor. The at least one control signal, of which the shape is restored by the restoring unit, may also comprises the capacitance select signal. It should be appreciated by the skilled person that one or more secondary storage capacitors can be used, that may or may not be individually selectable.

The image sensor tile may comprise read-out circuitry for reading out a selected row of pixels. To this end, each pixel may comprise a select transistor for selecting, in response to a pixel select signal, that pixel to be read out by the read-out circuitry. In this case, the at least one control signal, of which the shape is restored by the restoring unit, may also comprise the pixel select signal.

At least one of the select transistor, the first storage capacitor, the second storage capacitor, and the reset transistor are arranged in or forms the light insensitive part. In addition, the photosensitive diode is preferably arranged in or forms the photosensitive part.

The image sensor tile may further comprise a scintillator layer for converting X-rays into visible light that can be detected by the photosensitive pixel(s). For example, the converted X-rays may have a wavelength that corresponds to the photosensitive diode. However, the present invention not excludes embodiments wherein the X-rays are directly detected by the photosensitive diode, or other X-ray sensitive component.

The row driver may be configured to output the control signal(s) having a pulse shape, and the restoring unit may be configured to restore the shape of the control signal to this pulse shape, preferably with respect to reset, rise and/or fall times. Typically, the control signals are logic signals varying between a logic high and logic low value. However, as these signals propagate along the row of pixels, shape deterioration may occur causing for instance a strong reduction in steepness of the edges of the logic signal or a variation in the high or low values. These adverse properties are corrected, at least to a large extent, by the restoring unit.

The restoring unit(s) can be arranged in one pixel instead of being distributed over a plurality of preferably adjacently arranged pixels. Moreover, the restoring unit(s) can be arranged in each pixel of the plurality of pixels. In this latter case, each pixel in the pixel block would be identical.

The restoring unit could comprise a buffer. This buffer could comprise a pair of serially connected inverters. This implementation is advantageous as it uses components that are easily implemented in the technology that may be used for manufacturing the image sensor tile.

The pixels can be CMOS based. In this case, the above-mentioned buffer can be realized as a cascade of two CMOS inverters. These components do not require much area to be implemented.

Each pixel may comprise a pixel guard ring for isolation between adjacent pixels. The pixel guard ring extends down to a subsurface of the substrate of the semiconductor and is formed around each pixel to insulate further the respective pixel from noise generated by other pixels and/or components formed over the substrate. In this case, at least a part of the restoring unit, the buffer and/or inverter, for instance a PMOST or NMOST can be arranged in the pixel guard ring.

According to a second aspect, the present invention provides an image sensor comprising the image sensor tile as defined in any of the previous claims. This image sensor may comprise a scintillator layer as described above.

Next, the invention will be described in more detail by referring to the appended drawings, wherein.

Figure 3A:
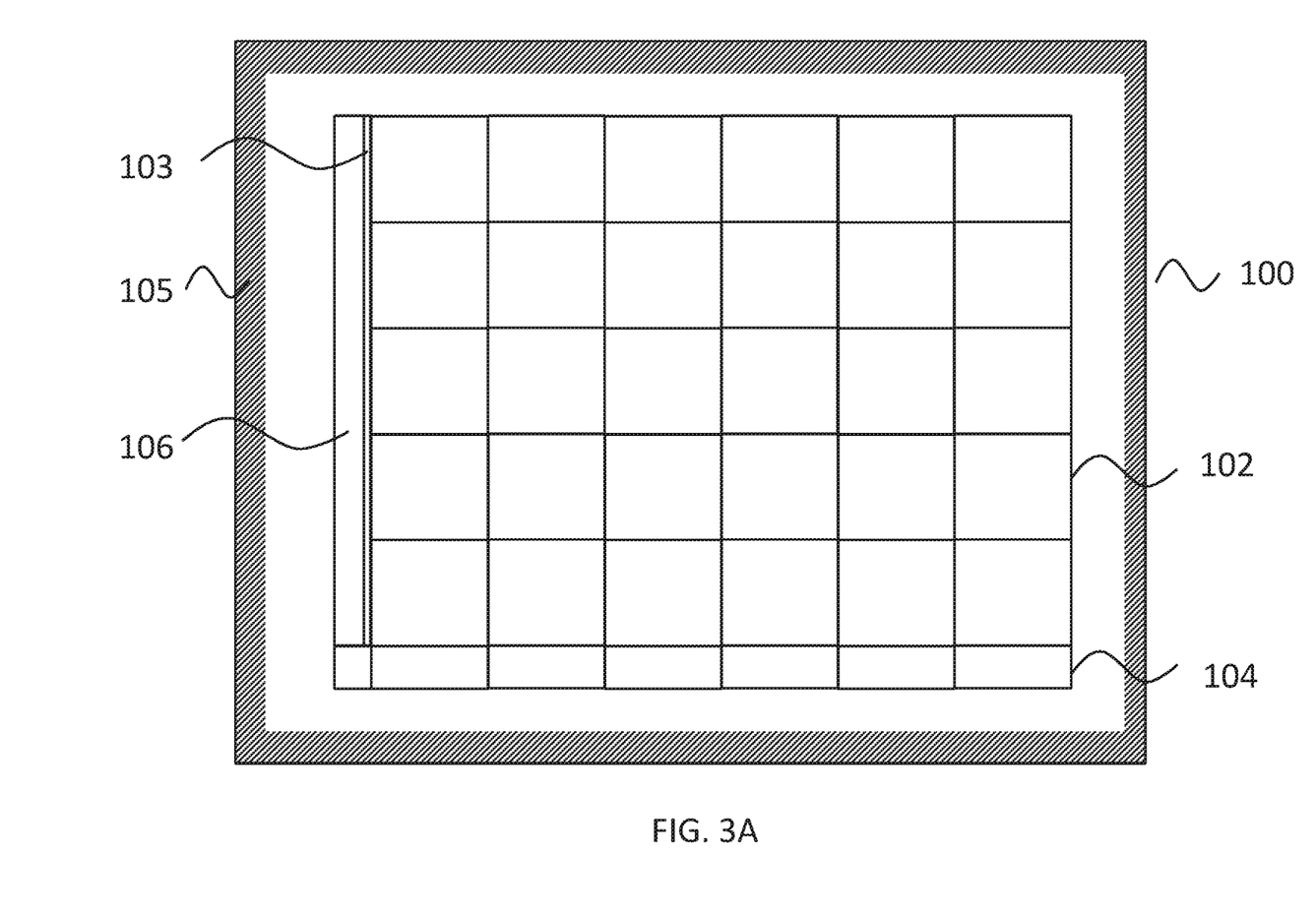
FIGS. 3A and 3B illustrate an embodiment of an X-ray sensor tile according to the present invention and a reticle used for realizing such tile, respectively.

FIG. 3A illustrates an X-ray sensor tile 100 according to an embodiment of the present invention which comprises a repetitive arrangement of identical pixel blocks 102. Each pixel block 102 comprises a plurality of pixels. As such a pattern of pixels is formed having rows and columns.

Similar to tile 1 in FIG. 1A, tile 100 comprises a sealing ring 105, and read-out circuitry 104 for reading out a selected row. However, unlike row drivers 3 in FIG. 1A, row drivers 103 are arranged outside of pixel blocks 102.

Figure 3B:
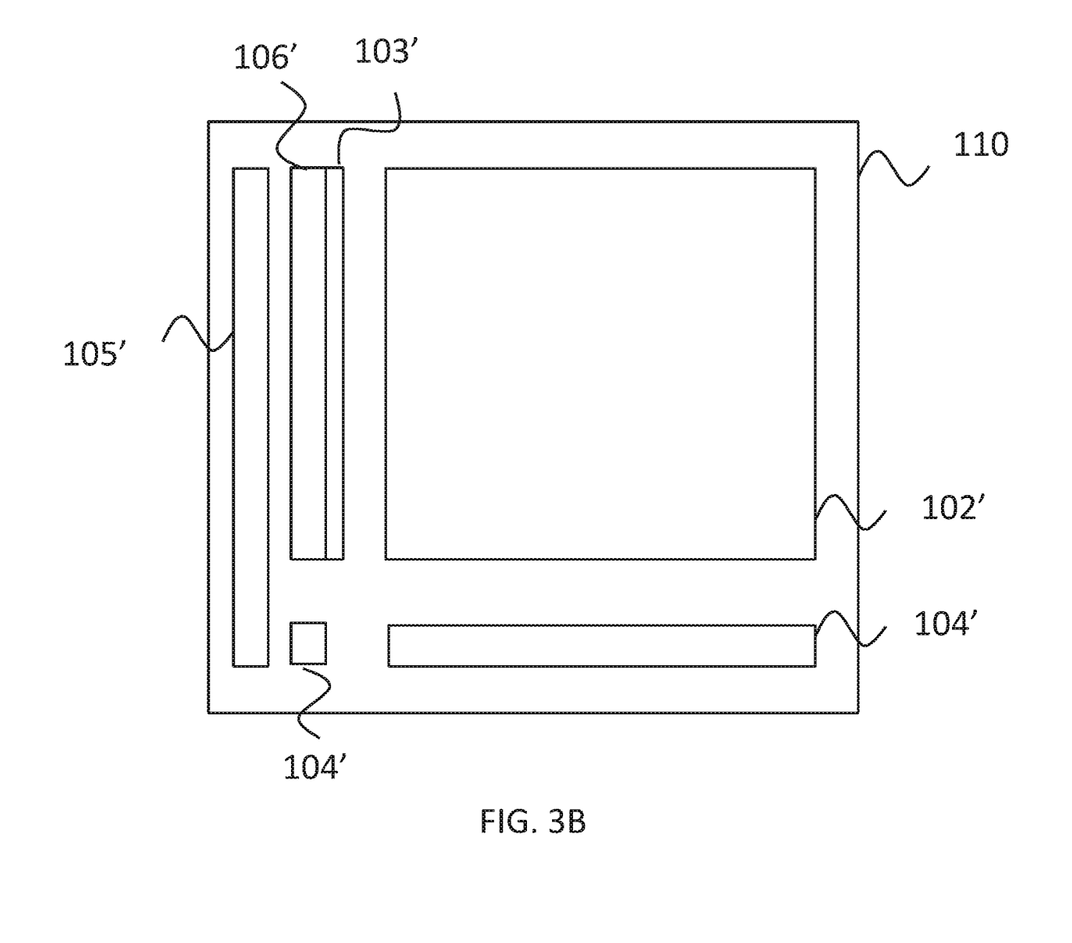

FIG. 3B illustrates a possible reticle 110 that can be used to define a layer or processing step of tile 100. This reticle comprises a region 102' having structures for defining pixel block 102, structures 104' for defining read-out circuitry 104, and structures 105' for defining sealing ring 105. Unlike reticle 10 in FIG. 1B, region 102' does not comprise structures for defining row drivers 103. Instead, structures 103' are arranged spaced apart from region 102'. Structures 103' may be arranged next to structures 106', which are used for defining blocks 106 of one or more pixels that are similar to the pixels defined by structures 102, see FIG. 3A. It is noted that structures 105', structures 106' and structures 103' can also be combined into a single block on the reticle. The pixels defined by structures 106' are advantageous if the X-ray sensor comprises butted sensor tiles, for example a pair of horizontally butted sensor tiles 100. Typically, when tiles are butted, a so-called butting gap exists of one or more pixel columns wide. In these butting gaps, no photosensitive elements can be arranged due to the physical distance between pixels on the different adjacent tiles. These butting gaps will introduce dark lines in the resulting X-ray image which must be corrected. The butting gaps are generally not visible in the output x-ray image, as they are a physical separation of a single or more pixel columns wide. The physical gap, i.e. the missing pixel column(s)), has to be inserted/filled with non-existing information by averaging using software algorithms. In case row drivers 103 would have been arranged at the edge of tile 100, an even larger area would exist that has no to little photosensitivity. By including pixel blocks 106, this problem can be alleviated.

Although FIG. 3A illustrates a particular arrangement of pixels blocks and row driver blocks, the skilled person should appreciate that the present invention is not limited thereto. For instance, denoting a pixel block by P, a first type row driver block by D, a second type row driver block by D*, the following arrangements form a non-limiting collection of exemplary arrangements in accordance with the present invention:

1. D-P-P-P-D
2. D-P-D-P-D
3. P-P-P-D
4. D-P-P-D*
5. D*-P-P-D*
6. D-P-D-P-D*
7. P-P-P-D*
8. P-D-P-D*
9. P-P-D-P-P
10. P-D-P-D-P

Here, D* differs from D in that D* comprises photosensitive pixels, such as pixel blocks 106 and similar to those in pixel block P, in addition to the row drivers. These blocks allow several tiles to be adjacently arranged, i.e. a butted tile configuration, without causing a too large a block of photo-insensitive elements that could result in image artefacts.

Figure 4A:
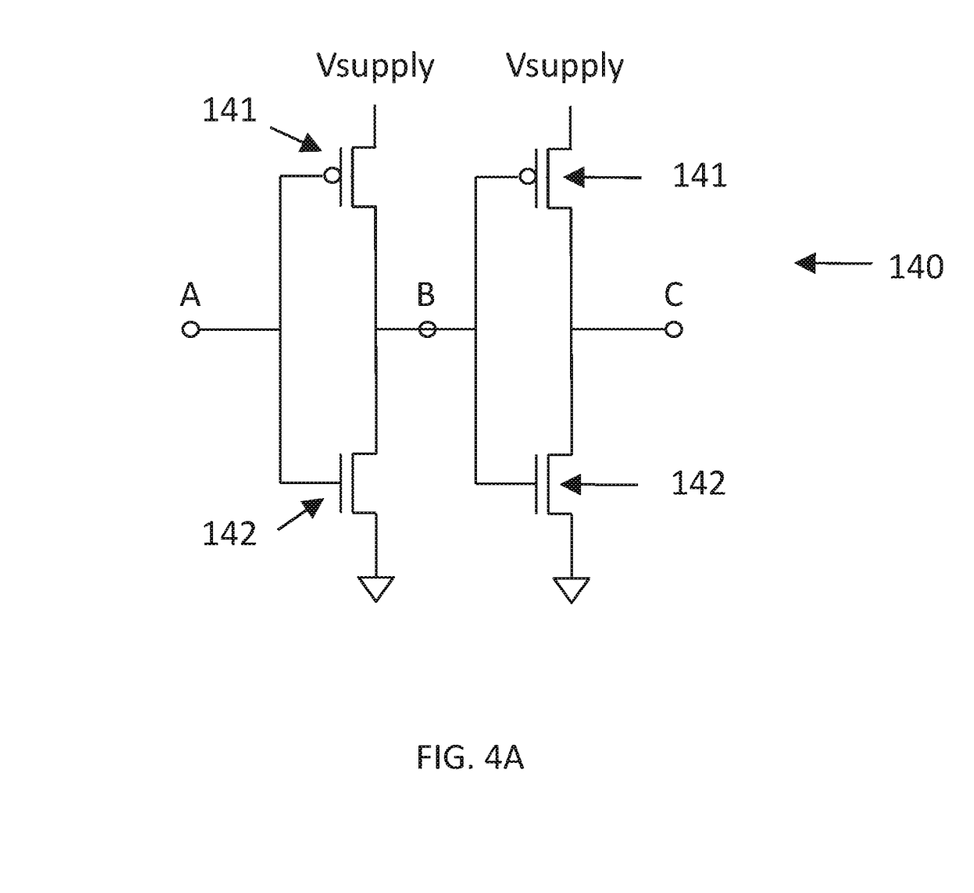
FIGS. 4A and 4B illustrate an embodiment of a signal restoring unit used in the embodiment of FIG. 3A and corresponding signal levels.

FIG. 4A illustrates an embodiment of a restoring unit 140 that can be used in tile 100. This unit comprises a CMOS buffer that is implemented here as two serially connected inverters. Each inverter comprising a PMOST 141 and a NMOST 142. In the same figures, nodes A, B, and C are indicated.

Figure 4B:
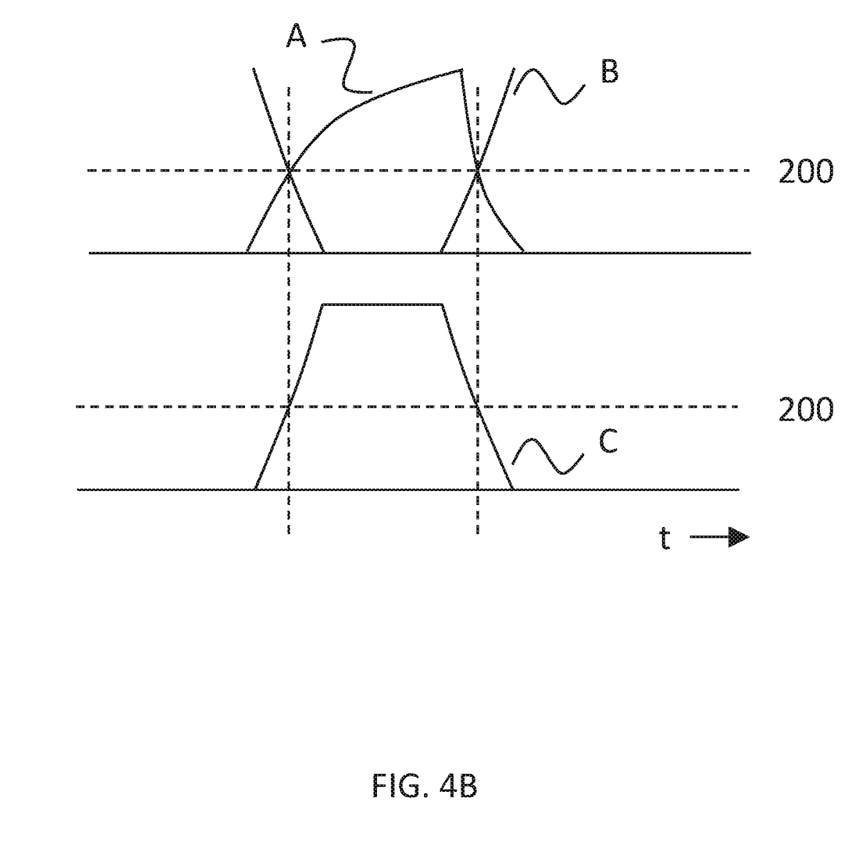

FIG. 4B illustrates a possible shape of a control signal that is fed to node A of restoring unit 140. As can be seen in FIG. 4B, the shape of this control signal is strongly deteriorated when compared to its initial shape, which is a logic signal that varies between a logic high and logic low value. More in particular, the rising edge and falling edge of the signal are not as steep as they should be. In addition, a signal variation can be observed in the middle of the pulse.

The first inverter inverts this signal resulting in a shape B. Then, the second inverter inverts the output of the first inverter, resulting in a shape C that closely corresponds to the shape of the original outputted control signal.

Restoring the control signals prevents issues with variation in integration times and the corresponding variation in light output, and ensures a temporal consistency when selecting or resetting the pixels in a given row. In addition, compared to known image sensor tiles, it is possible to reduce the delay and/or settling times that have to be used after applying the control signals allowing speeding up readout times and framerates. This allows tile 100 to operate with a limited amount of row drivers for each row. Here, it is noted that tile 100 could comprise an additional row driver arranged at the opposite side of a row. Also this row driver would be arranged outside of the pixel blocks.

As can be appreciated from the description above, the present invention is particularly well suited for implementation in large area image sensor devices and/or tiles, which are fabricated using for instance 1D/2D stitching techniques. The restoring unit ensures proper transfer of the control signals, despite the size of the sensor and/or tile, without degrading image quality of the raw image.

It should be apparent to the skilled person that although the present invention has been described using detailed embodiments thereof, the scope of the present invention is not limited to these embodiments. Instead, various modifications are possible without deviating from the scope of the invention which is defined by the appended claims.

The invention claimed is:

1. An image sensor tile, comprising:
    a plurality of identical pixel blocks, each pixel block comprising a plurality of pixels that are arranged in a pattern of rows and columns;
    a row driver block comprising a plurality of row drivers, each row driver in said row driver block being configured for providing at least one logic control signal to pixels that are arranged in a row that is associated with that row driver;
    wherein each pixel block comprises, for each pixel row, at least one restoring unit that is arranged in a single pixel in that row or at least one restoring unit that is distributed over pixels in that row, said at least one restoring unit being configured to restore a shape of the at least one control signal.

2. The image sensor tile of claim 1, wherein at least one pixel in each pixel block is photosensitive.

3. The image sensor tile of claim 1, wherein each row driver block comprises, per row, a plurality of further pixels that are substantially identical to the pixels in the pixel blocks, wherein the row driver for that row is further configured for providing at least one logic control signal to said further pixels.

4. The image sensor tile of claim 1, wherein the row driver block corresponds to a first sub-field of a reticle set and wherein the pixel blocks correspond to a second sub-field of that same reticle set, different from the first sub-field.

5. The image sensor tile of claim 1, wherein the image sensor tile comprises an arrangement of adjacently arranged pixel blocks, wherein a row driver block is arranged on at least one side of said arrangement.

6. The image sensor tile of claim 1, wherein the image sensor tile comprises an arrangement of a row driver block that is adjacently arranged to a pixel block on either side the of the row driver block.

7. The image sensor tile of claim 1, wherein the image sensor tile comprises an alternating arrangement of a pixel block and a row driver block.

8. The image sensor tile of claim 1, wherein each row driver block is configured to provide a plurality of logic control signals, wherein a restoring unit is arranged for each logic control signal or wherein the restoring unit is configured to restore the shape of each control signal.

9. The image sensor tile of claim 1, wherein each pixel comprises a light-sensitive part and a part that is substantially insensitive to light, wherein the restoring unit is arranged in the light insensitive part of said one or more pixels.

10. The image sensor tile of claim 9, wherein each pixel comprises:
a photosensitive diode;
a first storage capacitor for receiving electric charges from the photosensitive diode; and
a reset transistor for resetting, in response to a reset signal, a voltage at one of the terminals of the storage capacitor to a predefined voltage;
wherein said at least one control signal comprises said reset signal.

11. The image sensor tile of claim 10, wherein each pixel comprises:
a second or multiple switchable storage capacitor(s) that can be switched, in response to a capacitance select signal, in parallel to said first storage capacitor;
wherein said at least one control signal comprises said capacitance select signal.

12. The image sensor tile of claim 10, wherein the X-ray sensor tile comprises read-out circuitry for reading out a selected row of pixels, wherein each pixel comprises:
a select transistor for selecting, in response to a pixel select signal, said pixel to be read out by the read-out circuitry;
wherein said at least one control signal comprises said pixel select signal.

13. The image sensor tile of claim 12, wherein at least one of the select transistor, the first storage capacitor, the second storage capacitor, and multiple capacitors, and the reset transistor are arranged in the light insensitive part, and wherein the photosensitive diode is arranged in the photosensitive part.

14. The image sensor tile of claim 1, wherein the row driver is configured to output said control signal(s) having a pulse shape, and wherein the restoring unit is configured to restore the shape of the control signal to said pulse shape with respect to reset, rise and/or fall times.

15. The image sensor tile of claim 1, wherein the restoring unit(s) is(are) distributed in one pixel.

16. The image sensor tile of claim 1, wherein the restoring unit(s) is(are) arranged in each pixel of the plurality of pixels.

17. The image sensor tile of claim 1, wherein the restoring unit comprises a buffer.

18. The image sensor tile of claim 17, wherein the buffer comprises a pair of serially connected inverters.

19. The image sensor tile of claim 1, wherein the pixels are CMOS based.

20. The image sensor of claim 19, wherein each pixel comprises a pixel guard ring for isolation between adjacent pixels, wherein at least a part of the restoring unit is arranged in the pixel guard ring.

21. The image sensor of claim 1, further comprising a scintillator layer for converting X-rays into visible light that can be detected by the photosensitive pixel(s).

22. An image sensor comprising the image sensor tile recited in claim 1.

* * * * *